(12) United States Patent
Beaven

(10) Patent No.: US 9,668,725 B2
(45) Date of Patent: Jun. 6, 2017

(54) LAPAROSCOPIC WOUND CLOSURE DEVICE

(71) Applicant: Richard B. Beaven, Covington, KY (US)

(72) Inventor: Richard B. Beaven, Covington, KY (US)

( * ) Notice: Subject to any disclaimer, the term of this patent is extended or adjusted under 35 U.S.C. 154(b) by 190 days.

(21) Appl. No.: 14/667,025

(22) Filed: Mar. 24, 2015

(65) Prior Publication Data

US 2016/0278763 A1 Sep. 29, 2016

(51) Int. Cl.
 *A61B 17/04* (2006.01)
 *A61B 17/00* (2006.01)
 *A61B 17/34* (2006.01)
 *A61B 90/00* (2016.01)

(52) U.S. Cl.
 CPC ...... *A61B 17/0469* (2013.01); *A61B 17/0057* (2013.01); *A61B 17/0482* (2013.01); *A61B 17/3417* (2013.01); *A61B 17/3421* (2013.01); *A61B 2017/00637* (2013.01); *A61B 2017/00663* (2013.01); *A61B 2017/3445* (2013.01); *A61B 2090/062* (2016.02)

(58) Field of Classification Search
 CPC ............ A61B 17/0057; A61B 17/0469; A61B 17/0482; A61B 17/0483; A61B 17/0485; A61B 2017/00637; A61B 2017/00663; A61B 2017/047; A61B 2017/0472; A61B 2090/062
 See application file for complete search history.

(56) References Cited

U.S. PATENT DOCUMENTS

| | | | |
|---|---|---|---|
| 2,717,599 A | | 2/1952 | Huber |
| 4,553,543 A | * | 11/1985 | Amarasinghe ......... A61B 17/04 606/148 |
| 5,354,279 A | * | 10/1994 | Hofling ............. A61M 25/0069 604/164.12 |
| 5,368,601 A | | 11/1994 | Sauer et al. |
| 5,419,777 A | * | 5/1995 | Hofling .................. A61B 18/24 128/831 |
| 5,496,332 A | * | 3/1996 | Sierra ................ A61B 17/0057 606/139 |
| 5,507,755 A | | 4/1996 | Gresl et al. |
| 5,507,757 A | | 4/1996 | Sauer et al. |
| 5,507,758 A | | 4/1996 | Thomason et al. |
| 5,509,900 A | * | 4/1996 | Kirkman ........... A61M 25/0082 604/104 |
| 5,700,273 A | * | 12/1997 | Buelna ................... A61B 17/04 606/144 |

(Continued)

*Primary Examiner* — Ryan J Severson
(74) *Attorney, Agent, or Firm* — Hasse & Nesbitt LLC; Ronald J. Richter

(57) ABSTRACT

A laparoscopic wound closure device includes an elongated body portion including a proximal end, a distal end, and a pair of vertical suture channels. Each vertical suture channel has an entrance at the proximal end and an exit near the distal end for passing a suture needle through, and travels parallel to the longitudinal axis of the body portion of the device. The vertical suture channels are designed to cause a suture needle to deflect laterally as it exits the wound closure device. The wound closure device can be an obturator or a sheath of a trocar assembly, and can be used to inject local anesthetic at the conclusion of surgery.

18 Claims, 6 Drawing Sheets

(56) References Cited

U.S. PATENT DOCUMENTS

| | | | | |
|---|---|---|---|---|
| 5,814,065 | A * | 9/1998 | Diaz | A61B 17/0469 112/169 |
| 5,954,734 | A | 9/1999 | Thomason et al. | |
| 6,183,485 | B1 | 2/2001 | Thomason et al. | |
| 6,743,241 | B2 | 6/2004 | Kerr | |
| 8,920,442 | B2 * | 12/2014 | Sibbitt, Jr. | A61B 17/0057 606/139 |
| 8,945,060 | B2 * | 2/2015 | Bunch | A61M 25/007 604/164.01 |
| 8,979,822 | B2 * | 3/2015 | Vogelbaum | A61M 25/0054 604/525 |
| 8,992,549 | B2 * | 3/2015 | Bennett, III | A61B 17/0057 606/144 |
| 9,155,532 | B2 * | 10/2015 | Surti | A61B 17/0057 |
| 9,241,707 | B2 * | 1/2016 | Roorda | A61B 17/0469 |
| 9,414,820 | B2 * | 8/2016 | Voss | A61B 17/0057 |
| 9,486,191 | B2 * | 11/2016 | Gianotti | A61B 17/0057 |
| 2006/0030868 | A1 | 2/2006 | Bennett, III | |
| 2006/0142784 | A1 * | 6/2006 | Kontos | A61B 17/00234 606/139 |
| 2007/0049968 | A1 * | 3/2007 | Sibbitt, Jr. | A61B 17/0057 606/213 |
| 2008/0033459 | A1 * | 2/2008 | Shafi | A61B 17/0057 606/144 |
| 2008/0294001 | A1 * | 11/2008 | Surti | A61B 17/0057 600/104 |
| 2011/0112557 | A1 | 5/2011 | Beeley | |
| 2011/0218568 | A1 * | 9/2011 | Voss | A61B 17/04 606/232 |
| 2013/0103057 | A1 | 4/2013 | Keating et al. | |

* cited by examiner

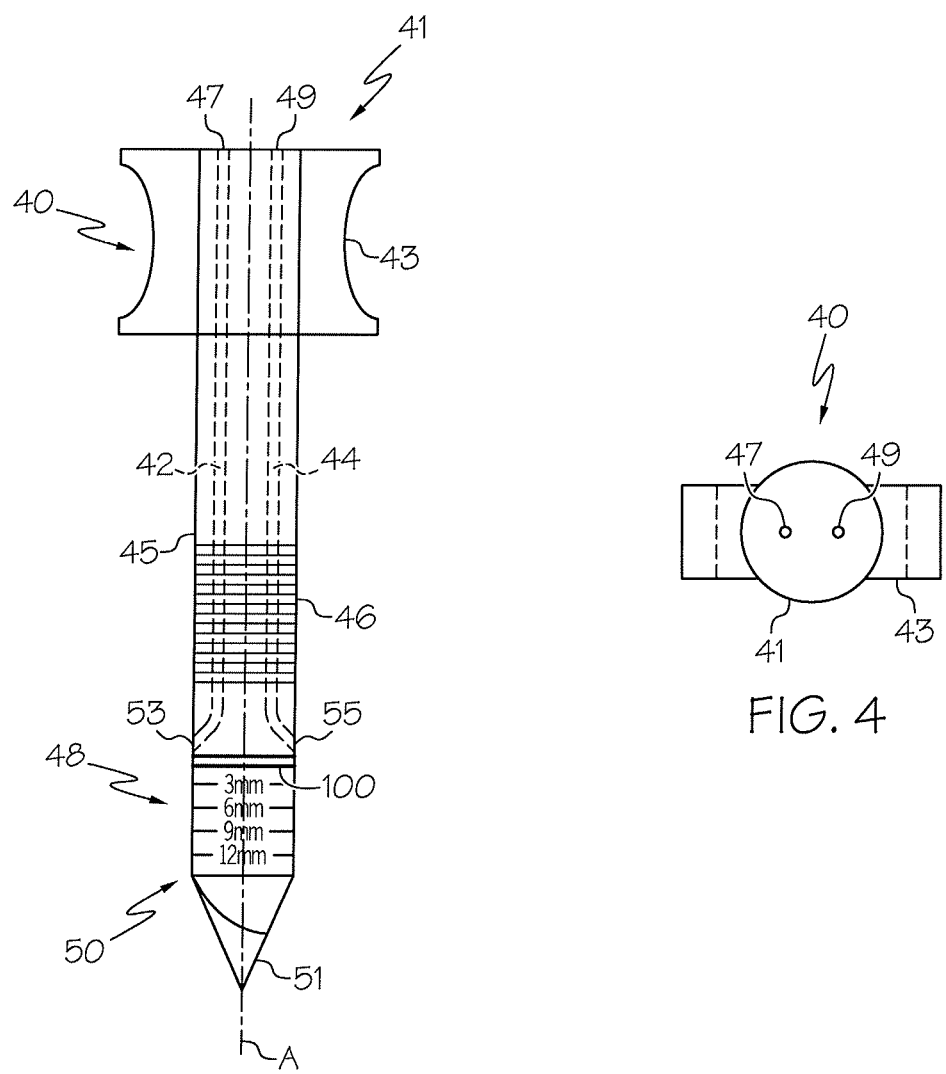

LAPAROSCOPIC WOUND CLOSURE DEVICE

FIELD OF THE INVENTION

The present invention relates generally to surgical suturing devices, and more particularly to abdominal suturing devices designed for closing laparoscopic puncture wounds.

BACKGROUND OF THE INVENTION

Laparoscopic surgery, or minimally invasive surgery, has replaced many standard invasive abdominal operations that require large incisions. Current laparoscopic surgical techniques include the creation of small incisions in the lateral abdominal wall, into which one or more surgical trocar assemblies or other similar puncturing devices are placed. A trocar assembly is typically comprised of an obturator having a puncturing distal end, and a sheath or cannula which is adapted to slide over the outer diameter of the obturator. The obturator and cannula are typically used together to puncture the lateral abdominal wall to gain access to the surgical site. Once the puncture is made, the obturator is removed from the hollow cannula creating a port for introducing and removing various surgical instruments. Scissors, dissectors, retractors, and biopsy instruments can be manipulated through a plurality of surgically placed ports, together with viewing devices such as endoscopes or laparoscopes, to perform surgery or diagnostic procedures. The intraperitoneal space is typically insufflated with pressurized carbon dioxide to provide more room and better exposure for viewing the anatomy and manipulating the instruments through the ports. This technology affords the patient considerably less pain and disfigurement, and a much faster recovery.

Upon completion of the laparoscopic procedure, the remaining trocar wounds are preferably sutured to close the wound. Closure of these wounds requires proper identification and closure of the underlying abdominal wall layers of connective tissue and muscle. If these fascial layers are not properly aligned and sutured closed, bowel herniation at the port site (a "port site hernia") can result, as well as the possibility of bowel strangulation or omental trapping. Because of the limited exposure provided by the very small size of the incision and the somewhat awkward, external access to the tissues surrounding the incision, proper closure of trocar wounds can be problematic and time consuming. Successful closure is also often further compromised by patient obesity and other factors.

When closing a lateral abdominal puncture wound the suturing needle should not only secure an optimal amount of tissue to prevent herniation but also avoid sensory and motor nerves present in the more superficial layers of the lateral abdominal wall. Specifically, the iliohypogastric, ilioinguinal and thoraco-abdominal nerves typically travel along a superficial fascial plane just beneath the internal oblique muscle, but not in the deeper layers that include the transversalis fascia, pre-peritoneal fat and the peritoneum. Thus, avoiding the more superficial layers of the lateral abdominal wall and passing the suture needle to close only the deeper fascial planes can avoid nerve entrapment or post-operative neuropathy, while still sufficiently closing the wound.

Current port site closure devices, such as that disclosed by U.S. Pat. No. 6,183,485 to Thomason et al. or U.S. Pat. No. 6,743,241 to Kerr, both of which are incorporated herein by reference in their entirety, close abdominal wall laparoscopic port sites via a "mass closure" device in order to prevent post-operative herniation. However, such mass closure devices use an approach in which the suture needle is passed indiscriminately and/or at an oblique angle through virtually all fascial layers of the lateral abdominal wall (see, e.g., FIG. 2, suture 32), which can lead to long term postoperative pain in the form of nerve entrapment, post-operative neuropathy and/or the need to surgically remove the suture.

While known abdominal wound closure devices may be useful for their intended purposes, it would be beneficial provide a wound closure device in which the suture needle avoids the superficial abdominal fascial layers containing nerves. There is also a need for an improved device and method for closing abdominal wound sites that can minimize the risk of nerve entrapment, post-operative neuropathy, puncture site herniation or other undesirable side effects of laparoscopic surgery. It would also be advantageous to provide a surgical device and method that can be utilized by surgeons having various skill levels.

SUMMARY OF THE INVENTION

Briefly stated, the wound closure device according to the various embodiments of this invention can decrease and/or eliminate the occurrence of nerve entrapment or post-operative neuropathy, while still securing an optimal amount of tissue to prevent post-operative herniation at the port site.

One aspect of the invention provides a wound closure device, the device comprising an elongated body portion including a proximal end, a distal end, and a pair of vertical suture channels, each vertical suture channel having an entrance at the proximal end and an exit near the distal end for passing a suture needle through, wherein the vertical suture channels travel parallel to the longitudinal axis of the body portion and cause the suture needle to deflect laterally as it exits the suture channel.

Another aspect of the invention provides an obturator of a trocar assembly for closing a trocar puncture wound, comprising an elongated body portion having a proximal end, a sharp distal end, and a pair of vertical suture channels, each vertical suture channel located within the body portion and having an entrance at the proximal end and an exit near the distal end for passing a suture needle through, wherein the vertical suture channels travel parallel to the longitudinal axis of the body portion and curve laterally within the body portion at the exit, thereby causing the suture needle to deflect laterally as it exits the suture channel.

Another aspect of the invention provides a sheath of a trocar assembly for closing a trocar puncture wound, comprising an elongated body portion having a proximal end, a distal end, a hollow passage extending longitudinally therethrough, and a pair of vertical suture channels, each of the vertical suture channels located along the outside of the sheath and having an entrance at the proximal end and an exit near the distal end for passing a suture needle through, wherein each of the vertical suture channels travels parallel to the longitudinal axis of the body portion and includes a deflection ridge at the exit that causes the suture needle to deflect laterally as it exits the suture channel.

The disclosed embodiments of the inventive device can be used for closing a laparoscopic puncture wound according to the steps of inserting the inventive device into the puncture wound; using a suture passing device to insert a suture needle through a first of the pair of vertical suture channels; piercing the deep fascial planes and avoiding the superficial layers of the lateral abdominal wall with the suture needle as it exits the first vertical suture channel; grasping the suture needle with a pickup instrument; passing the suture needle to the suture passing device, which has been passed through the second vertical suture channel; pulling the suture needle back through the second suture channel with the suture passing device; removing the wound closure device; and knotting the suture to close the wound.

The nature and advantages of the present invention will be more fully appreciated after reviewing the accompanying drawings, detailed description and claims.

BRIEF DESCRIPTION OF THE DRAWINGS

The accompanying drawings illustrate embodiments of the invention and, together with a general description of the invention given above, and the detailed description given below, serve to explain the principles of the invention.

FIG. 3 is cross-sectional plan view of a wound closure device according to one embodiment of the present invention;

FIG. 4 is a top, plan view of the wound closure device of FIG. 3;

DETAILED DESCRIPTION OF THE INVENTION

Figure 1:
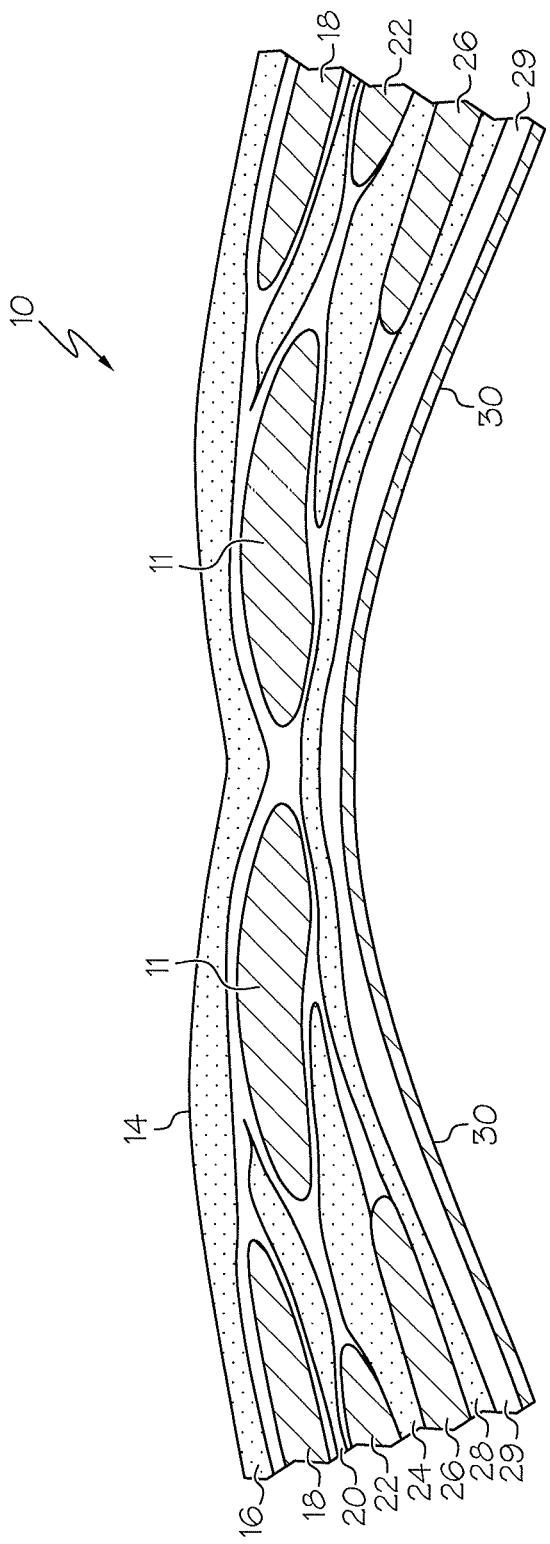
FIG. 1 is a cross-sectional view depicting the anatomy of the anterior abdominal wall.

FIG. 1 illustrates the general anatomy of the abdominal wall 10, which is initially covered by a layer of skin 14 and fat 16 and composed of pairs of muscles, notably the rectus abdominis 11, the external oblique 18, the internal oblique 22, and the transversus abdominis 26 muscles. These muscles and their fascial attachments, notably the external oblique fascia 20, the internal oblique fascia 24 and the transversalis fascia 28, interdigitate and unite to form a sturdy, protective musculofascial layer that gives strength and support to the anterolateral abdominal wall. Below the level of the transversalis fascia 28, a layer of pre-peritoneal fat 29 precedes the peritoneum 30. The pre-peritoneal fat 29 is of varying thickness from patient to patient, ranging from zero mm to about 20 mm depending on factors such as the body fat index of the patient. The peritoneum 30 is a smooth, serous membrane that forms the lining of the intraperitoneal space within the abdominal cavity.

Figure 2:
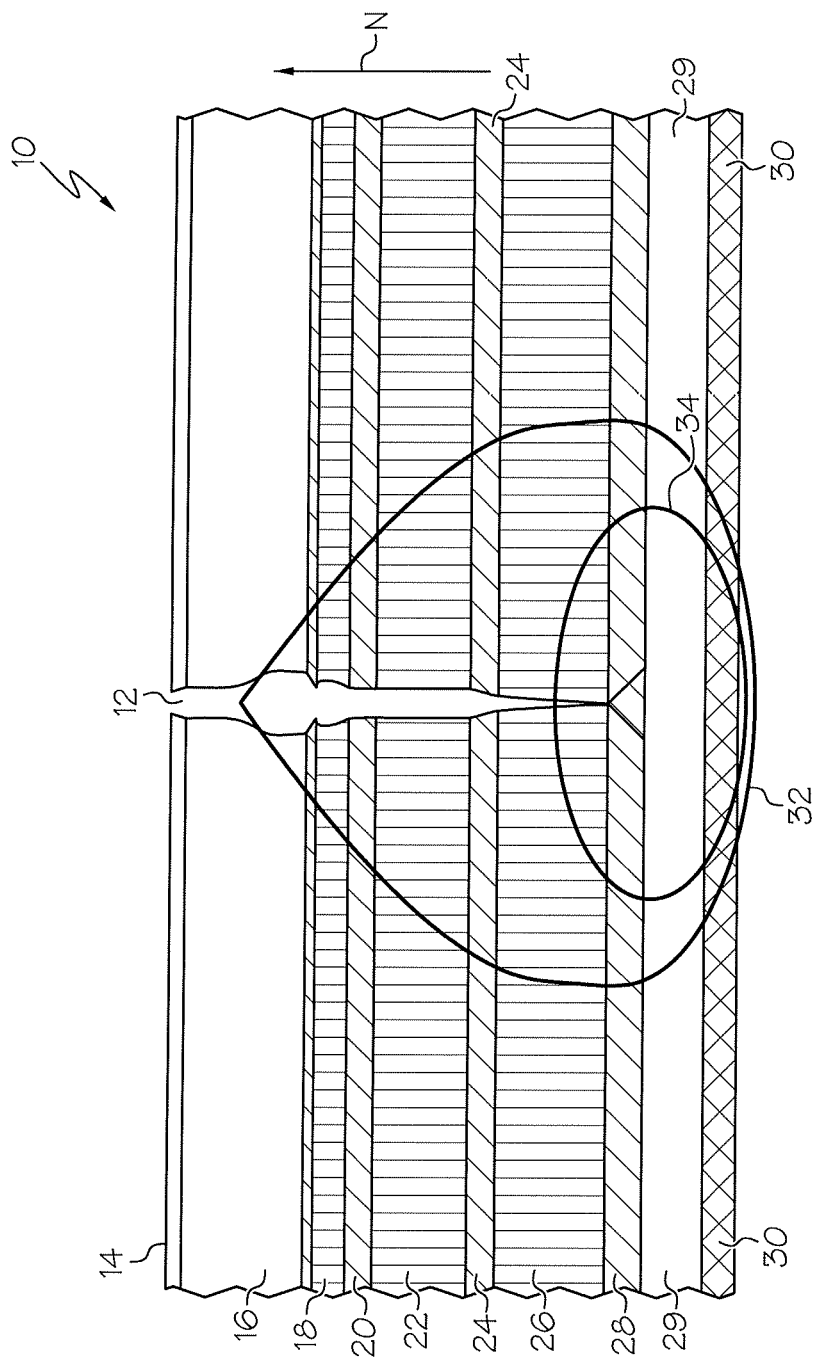
FIG. 2 is a cross-sectional side view showing two types of suture closure of a trocar wound through the lateral abdominal wall.

A trocar wound 12 that penetrates the above-noted layers of the lateral abdominal wall 10 is best seen in FIG. 2. During laparoscopic surgery a trocar wound 12 pierces the layers of the lateral abdominal wall, puncturing (in order) the skin 14, subcutaneous fat 16, the external oblique muscle 18, the external oblique fascia 20, the internal oblique muscle 22, the internal oblique fascia 24, the transversus abdominis muscle 26, the transversalis fascia 28, the pre-peritoneal fat 29 and the peritoneum 30. Sutures 32, 34 are shown, which are placed for either a mass closure 32 according to the prior art, or a deep closure 34 according to the present invention, in order to close the wound.

The arrow indicated by N in FIG. 2 indicates the superficial fascia/muscle layers, in which the majority of large sensory and motor nerves of the lateral abdominal wall are located. These layers generally comprise the internal oblique fascia 24 and higher (i.e. generally layers 18-24. Sutures placed by prior art mass closure devices, as shown by the placement of suture 32, passes the suture needle at an oblique angle through the superficial fascia and muscle layers indicated by arrow N, putting the iliohypogastric, ilioinguinal and thoraco-abdominal nerves at risk of entrapment and/or causing post-operative neuropathy. The present invention provides an improved wound closure device for deep placement of a suture 34, in which the suture needle is first passed vertically through the wound, within a vertical passage of the inventive closure device, and exits to penetrate the deep fascial planes only (i.e. the transversus abdominis muscle and deeper), avoiding the superficial layers N of the lateral abdominal wall. FIG. 2 shows a deep suture 34 of the present invention placed through the deep fascial planes (i.e. a portion of the transversus abdominis muscle 26, the transversalis fascia 28, the pre-peritoneal fat 29, and the peritoneum 30). Isolating the deep fascial planes and placement of a deep suture 34 in this manner can decrease and/or eliminate the occurrence of nerve entrapment or post-op neuropathy, while still securing an optimal amount of tissue to prevent herniation.

Figure 5:
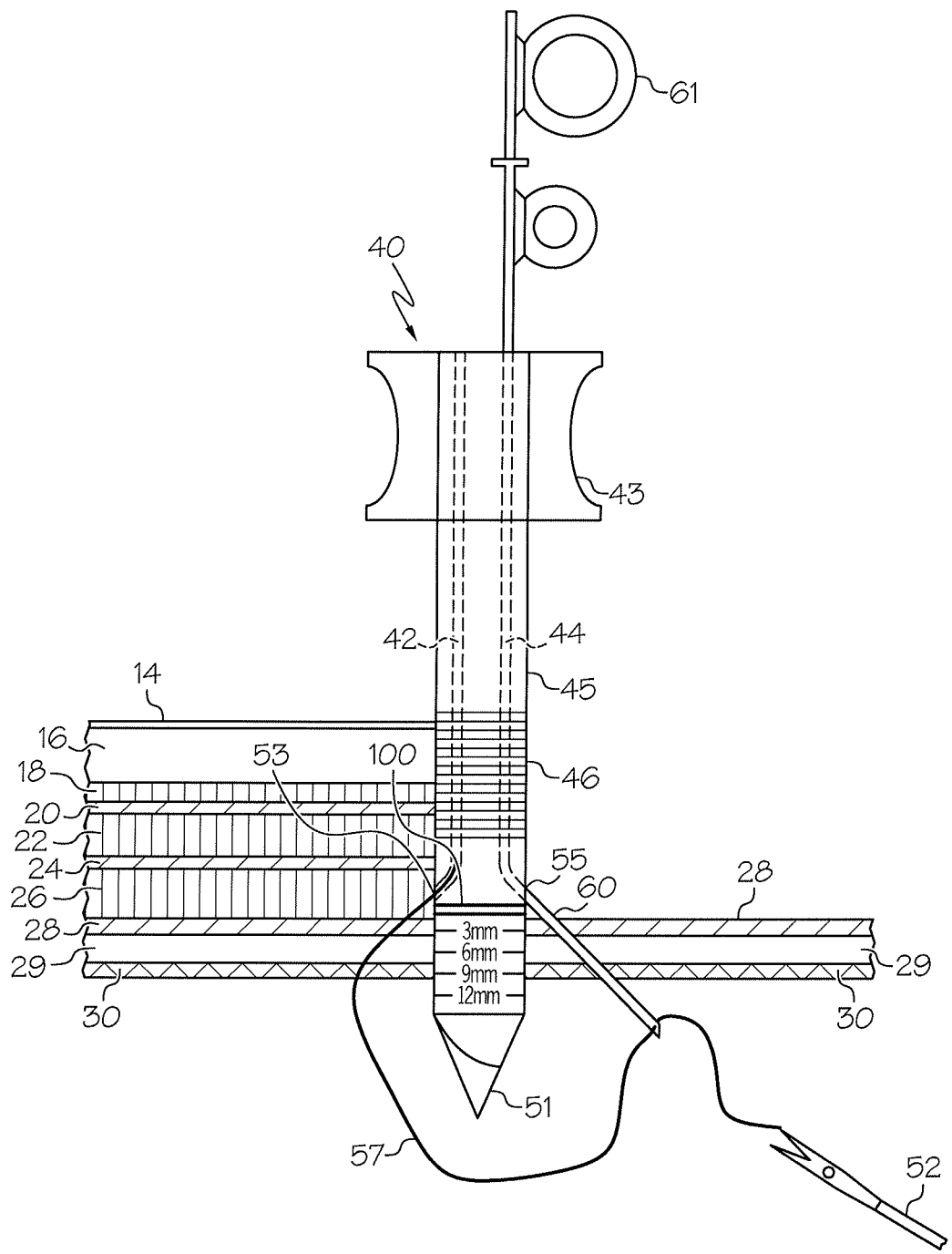
FIG. 5 is a cross-sectional view of the wound closure device of FIG. 3 placed in the trocar wound of FIG. 2.

One embodiment of the inventive device, as shown in FIGS. 3, 4 and 5, is a wound closure device 40 having an elongated body portion 45 including a proximal end 41 (with an ergonomic handle 43), a distal end 50 with a penetrating tip 51, and a pair of vertical suture channels, e.g. a first vertical suture channel 42 and a second vertical suture channel 44 located in and passing through the body 45 of the wound closure device 40. Each vertical suture channel 42, 44 has an entrance 47, 49 at the proximal end 41 and travels parallel to the longitudinal axis A-A of the body portion 45. As the vertical channels 42, 44 near the distal end 50 of the wound closure device they curve and exit the side of wound closure device via exits 53, 55. Exits 53 and 55 are located directly above the zero line 100 of depth markers 48, located at the distal end 50 of the device. The diameter of the body portion 45 of the wound closure device 40 should be chosen to fit the diameter of the wound 12 (see FIG. 2) created during surgery, and typically can be made to have a diameter of between 5 (five) mm and 20 (twenty) millimeters. If the wound closure device 40 is an obturator for a trocar assembly, then the diameter of the body portion 45 should be chosen to fit the diameter of the sheath of the trocar assembly.

The curve of the vertical suture channels 42, 44 at the distal end 50 of the wound closure device 40 will deflect and/or direct the suture needle laterally through the exits 53, 55. The channels 42, 44 can be curved at an angle of between 20° and 60° and preferably at an angle of between 30° and 45° from the longitudinal axis A-A of the wound closure device 40 to direct the suture needle laterally. Lateral deflection of the suture needle 60 by the channels 42, 44 in this manner causes the suture needle to take a large enough "bite" of the deepest fascial layers, i.e. the peritoneum 30, the pre-peritoneal fat 29 and the transversalis fascia 28, and optionally a deep portion of the transversus abdominis muscle 26. This approach can avoid the iliohypogastric, ilioinguinal and thoraco-abdominal nerves typically traveling closer to the skin surface 14, such as in the internal oblique fascia 24 running between the internal oblique muscle 22 and transversus abdominis muscle 26. Closing the peritoneum 30 and the transversalis fascia 28 is generally adequate for closing the puncture wound 12 and preventing the risk of herniation at the port site, nerve entrapment or post-operative neuropathy. Lateral deflection of the suture needle within the degree ranges noted above typically does not present a problem of bending the needle, since the needle can be made of a flexible metal as is known in the art.

Depth markers 48 located near the distal end 50 of the wound closure device 40 are used to determine the depth of suture placement (see FIG. 5). It is notable that the depth markers 48 do not represent how far down the suture is placed below the skin 14, but rather the depth markers 48 measure how far the suture is placed above the level of the peritoneum 30. The depth markers can be visualized by the surgeon via an endoscope inserted into the insufflated intraperitoneal space through a separate port. Zero line 100, as illustrated in FIGS. 3 and 5, is a depth marker that represents essentially 0.0 millimeters (mm) from its alignment with the peritoneum 30 to the suture exits 53, 55, which are located directly above the zero line 100. Thus, alignment of the zero line 100 with the peritoneum 30 will ensure that the suture needle at least passes through the peritoneum 30.

However, as noted above, the pre-peritoneal fat layer 29 (between the peritoneum 30 and the transversalis fascia 28) is variable in thickness from patient to patient. In obese patients, the depth markers 48 located below the zero line 100 can be placed at the level of the peritoneum 30 to ensure that the suture needle exits above the peritoneum 30 and above the layer of pre-peritoneal fat 29 to also pass through the transversalis fascia 28 and perhaps the deeper portion of the transversus abdominis muscle 26. The depth markers can be labeled in any manner desired (i.e. mm, inches, etc.), but typically should measure up to about 20 (twenty) mm from the zero line 100, thus allowing the surgeon to take into account the thickness of the patient's pre-peritoneal fat layer 29 and then judge how high above the peritoneum 30 the suture needle should be passed to adequately close the wound 12.

Stability ridges 46, as illustrated in FIGS. 3 and 5, are raised semi-circular ridges which typically protrude 1 mm to 2 mm from the outer circumference of the body portion 45. These ridges 46 hold the wound closure device 40 in place during use by virtue of the rough surface created by the raised ridges. The stability ridges 46 therefore increase friction between the wound tissue 12 and the device 40 to keep the device from sliding up and down during wound closure.

As can be appreciated from viewing FIG. 5, a flexible suture passing device 61 (as is known in the art) can be used to pass a suture needle 60 through the vertical suture channels 42 and 44. After the suture 57 and suture needle 60 are passed through the exit 53, thereby penetrating the deep fascial layers on one side of the device (e.g. the left side, as shown), the suture 57 is grasped with a pickup 52 from another port and "fed" to the suture needle 60 which has been passed via the passing device 61 through exit 55 of the opposite suture channel 44. The suture is then pulled back through the opposite suture channel and tied, with the surgical knot being placed deep into the puncture wound, generally at the level of the transversus abdominis muscle 26. This can be accomplished by the surgeon by initially removing the device 40 from the wound 12 once the suture 57 has been passed through the deep fascia on both sides of the wound 12. The surgeon can then tie the suture 57 into a surgical knot as the two suture ends exit the skin 14, and then push the knot down into the deeper fascial layers. A grasper or other type of knot passing device as is known in the art can be used to help tie the suture and tuck it into the wound.

Further, tying and knotting the suture at the level of the deep fascial layers, as shown by suture 34 in FIG. 2, can evert the fascial edges of the wound 12 towards the skin surface, thereby allowing the surgeon to isolate and thus better approximate the torn edges of the deep fascial layers.

Figure 6:
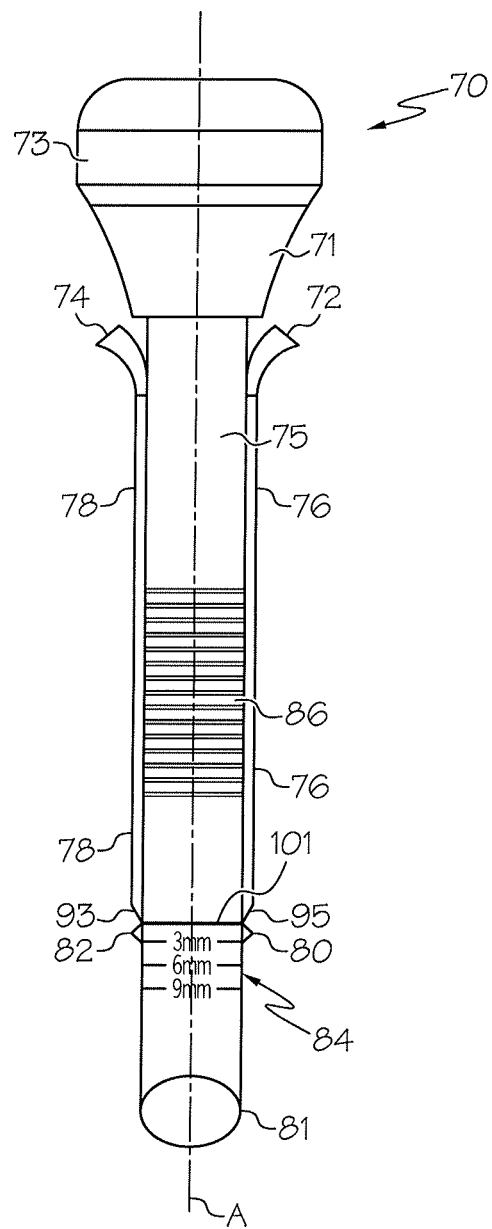
FIG. 6 is a cross-sectional plan view of a wound closure device according to another embodiment of the present invention.

One embodiment of the invention, illustrated in FIG. 6, provides a wound closure device 70 in the form of a sheath or hollow cannula. This sheath embodiment can not only be used to close the wound, but it can also serve as the "port" during the laparoscopy for insertion and manipulation of instruments. When the time comes to close the wound 12, the surgeon can simply remove the tools and close the wound using this port. As illustrated, the wound closure device 70 has an elongated body portion 75 including a proximal end 71 (with an ergonomic handle 73) and a hollow distal end 81. A pair of side ports 72, 74 form entrances at the proximal end 71 for a suture passing device, and lead to vertical suture channels 76, 78 which run externally to the body 75 of the sheath 70. Each vertical suture channel 76, 78 travels parallel to the longitudinal axis A-A of the body portion 75, but the channels end at exits 93, 95 as they near the distal end 81 of the sheath 70. Exits 93 and 95 are located directly above the zero line 101 of depth markers 84, located at the distal end 81 of the device. The diameter of the body portion 75 of the wound closure device 70 should be chosen to fit the diameter of the wound 12 (see FIG. 2) created during surgery, and typically can be made to have a diameter of between 5 (five) mm and 20 (twenty) millimeters. If the wound closure device 70 doubles as a sheath/port for a trocar assembly the diameter of the body portion 75 should be chosen to fit the diameter of the obturator of the trocar assembly.

Figure 7:
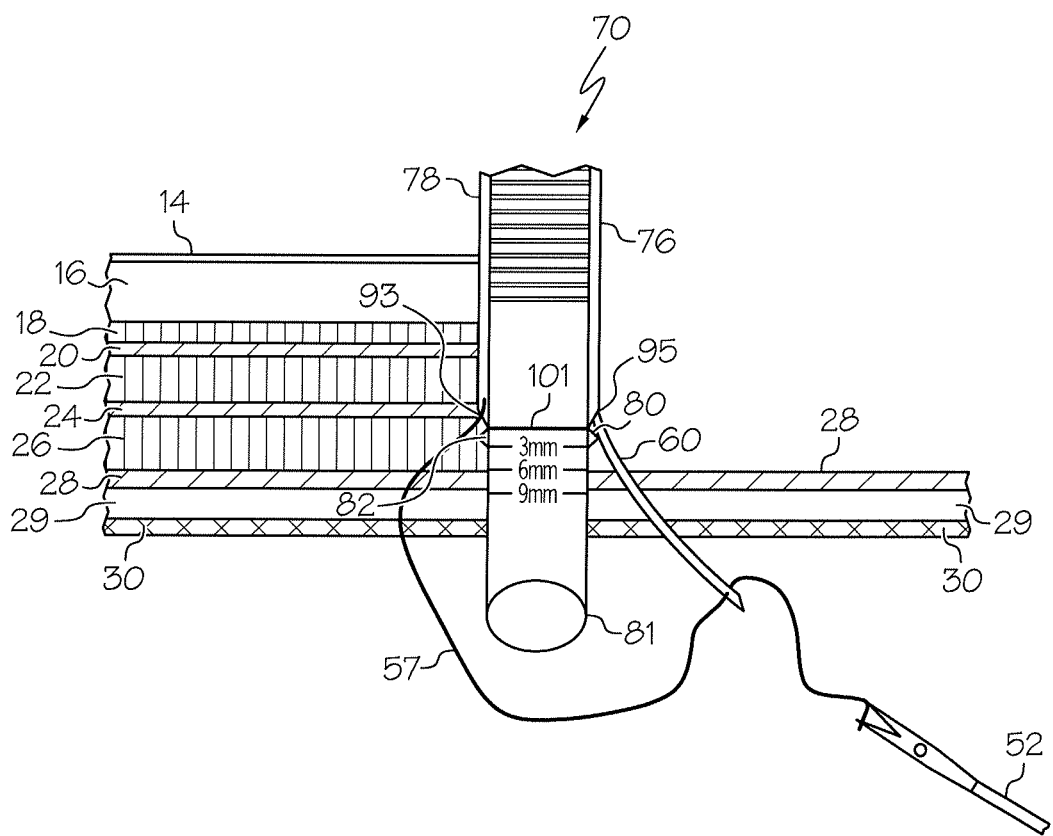
FIG. 7 is a cross-sectional view of the wound closure device of FIG. 6 placed in the trocar wound of FIG. 2.

Looking at FIG. 7, lateral deflection of the suture needle 60 by the deflection ridges 80, 82 as it passes through exits 93 or 95 causes the needle 60 to travel laterally to take a larger "bite" of the deepest fascial layers, while avoiding nerves typically traveling in the superficial abdominal layers. As noted above, avoiding the superficial layers of the lateral abdominal wall and passing the suture needle through the deeper fascial planes in this manner can prevent nerve entrapment or post-operative neuropathy, while also adequately closing the wound and preventing the risk of herniation at the port site.

The deflection ridges 80, 82 cause the needle to curve at an angle of between 20° and 60° and preferably at an angle of between 30° and 45° from the longitudinal axis A-A of the wound closure device 70 to direct the suture needle laterally. The deflection ridges 80, 82 can also include indentations (not shown) to ensure guiding of the suture needle laterally, and to prevent slippage of the needle anteriorly or posteriorly off of the side of the deflection ridge. For example, a semi-circular notch, score or indentation can be included on the top surface of each deflection ridge 80, 82 to aid in lateral guidance of the flexible suture passing device 61 and the needle 60 at the exits 93, 95 of the vertical suture channels 76, 78.

The zero line 101 and other depth markers 84 (see FIG. 6) located near the distal end 81 of the wound closure device are used to determine the depth of suture placement (see FIG. 7). It is notable that the depth markers do not represent how far down the suture is placed below the skin, but rather the depth markers 84 measure how far the suture is placed above the level of the peritoneum 30. The depth markers can be visualized by the surgeon via an endoscope inserted into the insufflated intraperitoneal space through a separate port. Zero line 101, as illustrated in FIGS. 6 and 7, is a depth marker that represents essentially 0.0 millimeters (mm) from its alignment with the peritoneum 30 to the suture exits 93, 95, which are located directly above the zero line 101. Thus, alignment of the zero line 101 with the peritoneum 30 will ensure that the suture needle at least passes through the peritoneum 30. However, as noted above, the depth markers 84 located beneath the zero line 101 on the device 70 can be placed at the level of the peritoneum 30 to ensure that the suture needle exits above the peritoneum 30 and above the layer of pre-peritoneal fat 29 to also pass through the transversalis fascia 28 and perhaps the deeper portion of the transversus abdominis muscle 26.

Stability ridges 86, as illustrated in FIG. 6, are raised semi-circular ridges which typically protrude 1 mm to 2 mm from the outer circumference of the body portion 75. These ridges 86 hold the wound closure device 70 in place during use by virtue of the rough surface created by the raised ridges. The stability ridges 86 therefore increase friction between the wound tissue 12 and the device 70 to keep the device from sliding up and down, both during use as a "port" during the procedure and during wound closure.

As can be appreciated from viewing FIG. 7, a suture needle 60 can be passed initially through a first vertical suture channel, such as suture channel 78, using a flexible suture passing device (e.g. 61, as seen in FIG. 5). After the suture 57 and suture needle 60 are passed through the exit 93, thereby penetrating the deep fascial layers on one side of the device (e.g. the left side, as shown), the suture 57 is grasped with a pickup 52 from another port and "fed" to the suture needle 60 which has been passed through exit 95 of the opposite suture channel 76. The suture is then pulled back through the opposite suture channel 76 and tied, with the surgical knot being placed deep into the puncture wound, generally at the level of the transversus abdominis muscle 26. This can be accomplished as described above.

The various embodiments of the inventive wound closure device disclosed herein can be manufactured as a separate surgical wound closure device 40, 70 inserted specifically for closure of the puncture wound, or it can be part of a trocar assembly, such as an obturator 40 (FIG. 3) or a sheath 70 (FIG. 6) of a trocar assembly that can be used during the surgery as well as during closure. The various embodiments of the wound closure device disclosed herein can also be used to inject an analgesic or anesthetic medication at the conclusion of the surgery, as the assembly is withdrawn from the incision. After suturing is completed, a spinal needle can be introduced via the exits 53, 55 of the vertical suture channels 42, 44 of the obturator 40 (see FIGS. 3-5), and/or the exits 93, 95 of the vertical suture channels 76 and 78 of the sheath 70 (see FIGS. 6 and 7). Medication such as local anesthetic can be placed into the tissues immediately affected by the trocar wound/tract, including punctured surfaces of the skin 14, external oblique muscle 18, the external oblique fascia 20, the internal oblique muscle 22, the internal oblique fascia 24, the transversus abdominis muscle 26, the transversalis fascia 28, the pre-peritoneal fat 29 and the peritoneum 30. Medication can be injected by needle and syringe to the surgical wound site via the vertical suture channels, beginning in the deeper tissues and ending at the skin surface as the surgeon removes the wound closure device 40, 70 from the wound 12.

In this manner, analgesic can be applied to the surgical wound site via the vertical suture channels as the inventive is device is removed at the conclusion of surgery, so that the local anesthetic is at maximum strength at the "actual" surgical site immediately post-operatively, and not at an "intended site" prior to incision and trocar placement, as is currently typically performed. The inventive device can therefore provide the ability to place post-operative analgesic or anesthetic medication where and when it is needed most. Placing analgesics prior to incision can lead to its application in the wrong place, with such early placement resulting in metabolization of the analgesic during the procedure, thereby lessening any post-operative pain relief.

The inventive device allows the suture to bypass and thus not incorporate the superficial layers of the lateral abdominal wall in the wound closure. The lateral diversion of the suture with a flexible suture passing device does not occur until the suture reaches the deeper layers of the abdominal wall. Such deep placement of the suture allows the surgeon to close only the deepest layers of the lateral abdominal wall in a specific manner, so as to avoid the nerves traveling in the more superficial layers. The depth markers are incorporated at the distal end of the device allow the surgeon to judge how far above the peritoneal surface the suture can be placed to compensate for patients having variable degrees of pre-peritoneal fat.

While the present invention has been illustrated by the description of particular embodiments in considerable detail, it is not intended to restrict or limit the scope of the appended claims to such detail. Additional advantages and modifications will be readily apparent to those skilled in the art without departing from the concept or scope of the invention.

What is claimed is:

1. A wound closure device for placement of a suture within the deep fascial layers of an abdominal wall puncture wound, the device comprising an elongated body portion including a longitudinal axis, a proximal end, a distal end, a plurality of depth markers located at the distal end, and a pair of vertical suture channels, each vertical suture channel having an entrance at the proximal end and an exit near the distal end for passing a suture needle through, wherein each suture channel travels parallel to the longitudinal axis of the body portion and is configured to cause the suture needle to deflect laterally at the suture channel exit, wherein each suture channel exit is located directly above a first of the plurality of depth markers, and wherein each of the plurality of depth markers indicates a distance from the suture channel exits.

2. The device of claim 1, wherein the device is a sheath for a trocar assembly, the sheath including a hollow passage extending longitudinally therethrough, and wherein each of the vertical suture channels are located along the outside of the sheath and include a deflection ridge at the exit for causing the suture needle to deflect laterally as it exits the suture channel.

3. The device of claim 2, wherein each of the vertical suture channels includes a side port forming the entrance at the proximal end.

4. The device of claim 1, further comprising stability ridges along the exterior of the body portion for holding the device in place during use.

5. The device of claim 1, wherein the distance from the suture channel exits indicated by one of the plurality of depth markers is the distance that the suture will be placed above the level of the peritoneum of the wound when the one depth marker is positioned at the level of the peritoneum.

6. The device of claim 1, wherein the deep fascial layers of the abdominal wall puncture wound include the peritoneum, the pre-peritoneal fat, and the transversalis fascia, and do not include the internal oblique fascia, the internal oblique muscle, the iliohypogastric nerve, the ilioinguinal nerve, the thoraco-abdominal nerve, the external oblique fascia, or the external oblique muscle.

7. The device of claim 6, wherein the deep fascial layers of the abdominal wall puncture wound also include a deep portion of the transversus abdominis muscle.

8. A sheath of a trocar assembly for closing an abdominal wall puncture wound by placement of a suture within the deep fascial layers of the wound, the sheath comprising an elongated body portion having a longitudinal axis, a proximal end, a distal end, a hollow passage extending longitudinally therethrough, a plurality of depth markers located at the distal end, and a pair of vertical suture channels, each of the vertical suture channels located along the outside of the sheath and having an entrance at the proximal end and an exit near the distal end for passing a suture needle through, wherein each of the vertical suture channels travels parallel to the longitudinal axis of the body portion and includes a deflection ridge at the exit for causing the suture needle to deflect laterally as it exits the suture channel, wherein each suture channel exit is located directly above a first of the plurality of depth markers, and wherein each of the plurality of depth markers indicates a distance from the suture channel exits.

9. The device of claim 8, wherein each of the vertical suture channels includes a side port forming the entrance at the proximal end.

10. The device of claim 8, further comprising stability ridges along the exterior of the body portion for holding the device in place during use.

11. The device of claim 8, wherein the distance from the suture channel exits indicated by one of the plurality of depth markers is the distance that the suture will be placed above the level of the peritoneum of the wound when the one depth marker is positioned at the level of the peritoneum.

12. The device of claim 8, wherein the deep fascial layers of the abdominal wall puncture wound include the peritoneum, the pre-peritoneal fat, and the transversalis fascia, and do not include the internal oblique fascia, the internal oblique muscle, the iliohypogastric nerve, the ilioinguinal nerve, the thoraco-abdominal nerve, the external oblique fascia, or the external oblique muscle.

13. The device of claim 12, wherein the deep fascial layers of the abdominal wall puncture wound also include a deep portion of the transversus abdominis muscle.

14. A method for closing a laparoscopic abdominal wall puncture wound by placement of a suture within the deep fascial layers of the wound, the method comprising the steps of:
 a) providing a device for placement of a suture within the deep fascial layers of an abdominal wall puncture wound while avoiding the superficial layers of the wound, the device comprising an elongated body portion including a longitudinal axis; a proximal end; a distal end; a plurality of depth markers located at the distal end; and a pair of vertical suture channels, each vertical suture channel having an entrance at the proximal end and an exit near the distal end for passing a suture needle through, wherein each suture channel travels parallel to the longitudinal axis of the body portion and is configured to cause the suture needle to deflect laterally at the suture channel exit, wherein each suture channel exit is located directly above a first of the plurality of depth markers, and wherein each of the plurality of depth markers indicates a distance from the suture channel exits;
 b) inserting the elongated body portion of the device into the puncture wound;
 c) positioning one of the plurality of depth markers at the level of the peritoneum of the puncture wound, wherein the distance from the suture channel exits indicated by the one depth marker is the distance that the suture will be placed above the level of the peritoneum;
 d) using a suture passing device to insert a suture needle through a first of the pair of vertical suture channels;
 e) piercing the deep fascial, planes and avoiding the superficial layers of the abdominal wall puncture wound with the suture needle as it exits the first vertical suture channel;
 f) grasping the suture needle with a pickup instrument;
 g) passing the suture needle to the suture passing device, which has been passed through the second vertical suture channel;
 h) pulling the suture needle back through the second suture channel with the suture passing device;
 i) removing the wound closure device; and
 j) knotting the suture to close the wound.

15. The method of claim 14, wherein the device is a sheath for a trocar assembly, the sheath including a hollow passage extending longitudinally therethrough, and wherein each of the vertical suture channels are located along the outside of the sheath and include a deflection ridge at the suture channel exit for causing the suture needle to deflect laterally.

16. The method of claim 14, further comprising the step of injecting an analgesic or anesthetic medication via the vertical suture channels as the device is removed from the wound.

17. The method of claim 14, wherein the suture needle pierces the peritoneum, the pre-peritoneal fat, and the transversalis fascia of the abdominal wall puncture wound, but does not pierce the internal oblique fascia, the internal oblique muscle, the iliohypogastric nerve, the ilioinguinal nerve, the thoraco-abdominal nerve, the external oblique fascia, or the external oblique muscle.

18. The method of claim 17, wherein the suture needle also pierces a deep portion of the transversus abdominis muscle.

* * * * *